(12) United States Patent
Wehling et al.

(10) Patent No.: US 7,815,897 B1
(45) Date of Patent: Oct. 19, 2010

(54) THERAPEUTIC EFFERVESCENT COMPOSITION

(75) Inventors: Fred Wehling, New Hope, MN (US); Mary Aldritt, Excelsior, MN (US); Robert E. Lee, Hudson, WI (US); Jason A. Kallestad, Minneapolis, MN (US)

(73) Assignee: Amerilab Technologies, Inc., Plymouth, MN (US)

( * ) Notice: Subject to any disclaimer, the term of this patent is extended or adjusted under 35 U.S.C. 154(b) by 1690 days.

(21) Appl. No.: 10/743,118

(22) Filed: Dec. 22, 2003

(51) Int. Cl.
  *A61K 9/46* (2006.01)
  *A61K 9/12* (2006.01)
(52) U.S. Cl. .......................... 424/44; 424/401; 424/466
(58) Field of Classification Search .................. 424/464, 424/466, 44, 401
  See application file for complete search history.

(56) References Cited

U.S. PATENT DOCUMENTS

| | | | | |
|---|---|---|---|---|
| 3,629,468 A | * | 12/1971 | Andersen | 424/44 |
| 3,772,431 A | * | 11/1973 | Mlkvy et al. | 424/44 |
| 4,471,871 A | * | 9/1984 | Rockliffe et al. | 206/205 |
| 4,627,972 A | * | 12/1986 | Gioffre et al. | 424/44 |
| 4,687,662 A | * | 8/1987 | Schobel | 424/44 |
| 5,993,854 A | * | 11/1999 | Needleman et al. | 424/466 |
| 6,197,338 B1 | | 3/2001 | Nürnberg et al. | |
| 6,280,775 B1 | | 8/2001 | Sasson et al. | |
| 6,506,713 B1 | | 1/2003 | Slavtcheff et al. | |
| 2003/0161875 A1 | * | 8/2003 | Murpani et al. | 424/465 |

* cited by examiner

*Primary Examiner*—Michael G Hartley
*Assistant Examiner*—Jagadishwar R Samala
(74) *Attorney, Agent, or Firm*—Allison Johnson, P.A.

(57) ABSTRACT

Disclosed is an effervescent composition that includes menthol, eucalyptus oil, and an effervescent agent and that dissolves in water to form a clear solution.

34 Claims, No Drawings

THERAPEUTIC EFFERVESCENT COMPOSITION

BACKGROUND

The invention relates to preparing therapeutic effervescent compositions for inhalation.

Essential oils and other aromatic materials have been used for centuries as aromatherapy agents. Eucalyptus oil, for example, has been used for relief from nasal congestion and as an expectorant. Menthol is often employed for its perceived cooling effects on the body and nasal passages.

Menthol and eucalyptus oil are often combined for use in aromatherapy and the combination takes a variety of forms. In one form, menthol and eucalyptus oil are combined with other ingredients in a petroleum base to form a vaporizing ointment, one example of which is a product that is commercially available under the trade designation VICKS VAPORUB. Eucalyptus oil and menthol have also been combined with a maltodextrin base and then formulated with other components into tablets that effervesce when placed in water.

Forming tablets of effervescent compositions that includes oils can lead to the release of chunks of the tablet as the tablet degrades in water. Many times the chunks do not fully dissolve. In addition, as the effervescent tablets degrade, an aesthetically undesirable residue (e.g., scum) can form on the surface of the water. The residue often includes oil, particulate, and, depending on the formulation of the effervescent composition, plant matter.

SUMMARY

In one aspect, the invention features an effervescent composition that includes menthol, eucalyptus oil, and an effervescent agent, the effervescent composition dissolving in water having a temperature of about 38° C. to a clear solution.

In one embodiment, effervescent composition is in the form of a tablet that includes an effervescent composition including menthol, eucalyptus oil, and an effervescent agent, the tablet dissolving in water having a temperature of at least 38° C. to form a clear solution.

In one embodiment, the composition includes from 0.5% by weight to about 10% by weight menthol. In another embodiment, the composition includes from 1% by weight to about 5% by weight menthol.

In other embodiments the composition includes from 0.5% by weight to about 10% by weight eucalyptus oil. In some embodiments the composition includes from 1% by weight to about 7% by weight eucalyptus oil.

In some embodiments the tablet has a hardness of at least 5 kilopounds. In other embodiments the tablet has a hardness of at least 15 kilopounds. In another embodiment the tablet has a hardness of at least 20 kilopounds.

In another embodiment the tablet dissolves in water having a temperature of about 38° C. in less than 120 seconds. In other embodiments, the tablet dissolves in water having a temperature of about 38° C. in less than 100 seconds. In some embodiments, the tablet dissolves in water having a temperature of about 38° C. in less than 120 seconds.

In one embodiment, the tablet further includes lubricant. In some embodiments, the lubricant includes sodium benzoate, polyethylene glycol, L-leucine, adipic acid, or a combination thereof.

In other embodiments, the tablet further includes magnesium oxide. In another embodiment, the tablet further includes pigment. In one embodiment, the tablet further includes flavor agent. In some embodiments, the tablet further includes sweetening agent. In other embodiments, the tablet further includes sorbitol.

In one embodiment, the tablet includes an effervescent composition that includes menthol, eucalyptus oil, and an effervescent agent, the tablet having a hardness of at least 10 kilopounds and dissolving in water having a temperature of about 38° C. in less than 120 seconds. In some embodiments, the tablet dissolves in water having a temperature of about 38° C. in less than 100 seconds. In other embodiments the tablet has a hardness of at least 15 kilopounds. In some embodiments the tablet has a hardness of at least 20 kilopounds.

In one embodiment, the effervescent composition is in the form of a powder.

In another aspect the invention features a package that includes air tight sealed packaging; and an effervescent composition (e.g., a tablet or a powder) disposed in the sealed packaging. In one embodiment, the package is free of puffing after storage at 45° C. for 24 hours.

In another aspect, the invention features an effervescent mouthwash that includes water, menthol, eucalyptus oil, and carbon dioxide.

In other aspects, the invention features a method of forming an aqueous effervescing composition, the method including dissolving an effervescent composition disclosed herein in water.

In another aspect, the invention features a method of treating a human, the method including dissolving in water to form a clear solution, and inhaling vapors emitted by the solution. In some embodiments, the method further includes gargling with the solution. In some embodiments, the water is at a temperature of at least 38° C. In other embodiments, the water is boiling water.

The present invention features an effervescent composition that emits therapeutic vapors when disposed in water and that dissolves to form a clear solution. The vapors include vapors of one or more therapeutic agents (e.g., menthol and eucalyptus). The vapors can have a therapeutic effect on the inhaler's respiratory tract.

The invention also features effervescent tablets that exhibit good integrity and hardness and dissolve relatively rapidly in water. The tablets also exhibit good stability over time.

Other features and advantages will be apparent from the following description of the preferred embodiments and from the claims.

GLOSSARY

In reference to the invention, these terms have the meanings set forth below:

The term "effervescent composition" as used herein means a composition that evolves gas bubbles when contacted with water.

DETAILED DESCRIPTION

The effervescent composition includes a volatile therapeutic agent and an effervescent agent. The effervescent composition dissolves rapidly in hot tap water and evolves vapors of the therapeutic agent, which are then available for inhalation by a user. Preferably vapor of the therapeutic agent and steam from the hot water evolve simultaneously from the aqueous composition. The effervescent composition is preferably in the form of a tablet (about 3.5 g) and dissolves to a visibly clear solution in hot tap water (e.g., at least 38° C.) in less than about 100 seconds.

The effervescent composition also exhibits good stability. The effervescent agent of an effervescent composition can decompose over time and evolve a gas such as carbon dioxide, which can cause the packaging in which the effervescent composition is located to expand, which is observed as "puffing". Packages of the effervescent compositions preferably are essentially free of puffing, or even free of puffing, after storage at room temperature for 24 hours, one month, for three months, for six months or even for one year.

Preferred volatile therapeutic agents include, e.g., menthol, eucalyptus oil, camphor, and combinations thereof. Useful sources of menthol include menthol crystals (e.g., U.S. Pharmacopeia (USP) grade menthol crystals). The effervescent composition preferably includes from about 0.5% by weight to about 10% by weight, from about 0.5% by weight to about 5% by weight, or even from about 1% by weight to about 2% by weight menthol.

Useful sources of eucalyptus oil include USP grade eucalyptus oil. The composition preferably includes from about 0.5% by weight to about 10% by weight, from about 1% by weight to about 7% by weight, or even from about 1.5% by weight to about 3% by weight eucalyptus oil.

The effervescent agent preferably is an effervescent couple that includes an acid and a base. The effervescent couple is activated when contacted with water, e.g., when the tablet is placed in a glass of water. The water liberates the acid and base and enables the acid and base to react with each other to produce carbon dioxide gas, which imparts carbonation to the aqueous composition. At least one component of the effervescent couple can also be an active agent. Examples of useful acids include citric acid, ascorbic acid, malic acid, adipic acid, tartaric acid, fumaric, succinic acid, sodium acid pyrophosophate, lactic acid, hexamic acid, and acid salts and acid anhydrides thereof, and mixtures thereof. Examples of useful acid anhydrides include citraconic anhydride, glucono-D-lactone, and succinic anhydride. Examples of useful acid salts include potassium bitartrate, acid citrate salts, sodium dihydrogen phosphate, disodium dihydrogen phosphate, sodium acid sulfite, and combinations thereof. Acid is present in the composition in an amount of from 10% by weight to about 60% by weight, from about 15% by weight to about 50% by weight, or even from about 25% by weight to about 40% by weight.

The base preferably is capable of generating carbon dioxide. Examples of suitable carbonate bases include sodium bicarbonate, sodium carbonate, sodium sesquicarbonate, potassium carbonate, potassium bicarbonate, calcium carbonate, magnesium carbonate, magnesium oxide, sodium glycine carbonate, L-lysine carbonate, arginine carbonate, zinc carbonate, zinc oxide and mixtures thereof. The base is present in the composition in an amount of from 10% by weight to about 60% by weight, from about 15% by weight to about 50% by weight, or even from about 25% by weight to about 40% by weight.

The effervescent composition can be in a variety of forms including, e.g., powder (e.g., a free flowing granulation), tablet, capsule, and pellet. Useful effervescent tablets have an initial hardness (i.e., a hardness immediately after manufacture) of at least 3 kilopounds (Kp), at least 4 Kp, from about 5 Kp to about 15 Kp, or even from about 5 Kp to about 10 Kp, as measured on a standard hardness tester fitted with a strain gauge, and a hardness 24 hours after manufacture of at least 5 Kp, at least 6 Kp, at least 10 Kp, at least 15 Kp, at least 20 Kp, or even from about 30 Kp to about 45 Kp.

The tablets can be formed to have any desired weight and dimension. Useful tablet weights include, e.g., from 0.5 gram to 15 gram, from 1 gram to 10 gram, from 2.5 gram to 5.5 gram, or even from 3 gram to 4 gram. Useful tablets are also formed with a diameter of at least 5 millimeters (mm), from 10 mm to about 70 mm, from 15 mm to about 50 mm or even from about 15 mm to about 25 mm, and a thickness of at least about 3 mm, at least 5 mm, no greater than 12 mm, no greater than 10 mm, or even no greater than 8 mm. Preferably the effervescent tablet dissolves in hot tap water in less than 300 seconds, less than 180 seconds, less than 120 seconds, less than 100 second, less than 80 seconds, or even less than 60 seconds. Preferably the tablet dissolves in water to a clear solution that is free of sediment and is free of surface residue (i.e., scum).

When in the form of a tablet or capsule, the composition preferably includes binder, lubricant, and combinations thereof. Examples of suitable binders include, e.g., starches, natural gums, cellulose gums, microcrystalline cellulose, methylcellulose, cellulose ethers, sodium carboxymethylcellulose, ethylcellulose, gelatin, dextrose, lactose, sucrose, sorbitol, mannitol, polyethylene glycol, polyvinylpyrrolidone, pectins, alginates, polyacrylamides, polyvinyloxoazolidone, polyvinylalcohols and mixtures thereof.

The composition includes a sufficient amount of binder to assist in holding the components of the composition together in the form of a tablet. Preferably binder is present in the composition in an amount of from 10% by weight to about 60% by weight, from about 15% by weight to about 50% by weight, or even from about 25% by weight to about 40% by weight.

Various lubricants are suitable for use in the composition including water dispersible, water soluble, water insoluble lubricants and combinations thereof. Preferred lubricants are water soluble. Examples of useful water soluble lubricants include sodium benzoate, polyethylene glycol, L-leucine, adipic acid, and combinations thereof. The composition can also include water insoluble lubricants including, e.g., stearates (e.g., magnesium stearate, calcium stearate and zinc stearate), oils (e.g., mineral oil, hydrogenated and partially hydrogenated vegetable oils, and cotton seed oil) and combinations thereof. Other water insoluble lubricants include, e.g., animal fats, polyoxyethylene monostearate, talc, and combinations thereof.

The effervescent composition preferably includes a sufficient amount of lubricant to enable the composition to be formed into tablets and released from a high speed tableting press in the form of a tablet. The effervescent composition includes water soluble lubricant in an amount of from 1% by weight to about 15% by weight, from about 1% by weight to about 12% by weight, from about 2% by weight to about 10% by weight, or even from about 3% by weight to about 8% by weight. Preferably the composition includes sodium benzoate in an amount of from 1% by weight to about 3% by weight and polyethylene glycol in an amount of from 1% by weight to about 5.5% by weight.

The effervescent composition preferably has less than 3% by weight water insoluble lubricants, less than 0.6% by weight water insoluble lubricants, or even no greater than 0.1% by weight water insoluble lubricants, and preferably no greater than 1% by weight oil, no greater than 0.5% by weight oil, no greater than 0.3% by weight oil, or even the effervescent composition is free of oil and other water insoluble lubricants.

The effervescent composition can also include other ingredients including, e.g., flavor agents, fillers, surfactants (e.g., polysorbate 80 and sodium lauryl sulfate), color agents including, e.g., dyes and pigments, and sweeteners.

Useful flavor agents include natural and synthetic flavoring sources including, e.g., volatile oils, synthetic flavor oils, flavoring aromatics, oils, liquids, oleoresins and extracts derived from plants, leaves, flowers, fruits, stems and combinations thereof. Useful flavor agents include, e.g., citric oils, e.g., lemon, orange, grape, lime and grapefruit, fruit essences including, e.g., apple, pear, peach, grape, strawberry, raspberry, cherry, plum, pineapple, apricot, and other fruit flavors. Other useful flavor agents include, e.g., aldehydes and esters (e.g., benzaldehyde (cherry, almond)), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodedenal (citrus, mandarin) and mixtures thereof.

Useful coloring agents include, e.g., food, drug and cosmetic (FD&C) colors including, e.g., dyes, lakes, and certain natural and derived colorants. Useful lakes include dyes absorbed on aluminum hydroxide and other suitable carriers.

Useful sweetening agents include stevia, sugars such as sucrose, glucose, invert sugar, fructose, ribose, tagalose, sucralose, malitol, erythritol, xylitol, and mixtures thereof, saccharin and its various salts (e.g., sodium and calcium salt of saccharin), cyclamic acid and its various salts, dipeptide sweeteners (e.g., aspartame), acesulfame potassium, dihydrochalcone, glycyrrhizin, and sugar alcohols including, e.g., sorbitol, sorbitol syrup, mannitol and xylitol, and combinations thereof.

The effervescent composition is preferably stored in an air tight, moisture-proof package including, e.g., sealed metal foil pouches, blister packs, and desiccant capped tubes. Useful packaging materials include, e.g., polymeric packaging (e.g., polyethylene and polypropylene), metal foils (e.g., aluminum), and combinations thereof.

A useful method of using the effervescent composition includes dissolving the composition in excess hot water to form an aqueous solution. A user can then inhale the vapors produced by the solution. Alternatively or in addition, the aqueous composition can be used as a mouthwash, rinse, or gargle composition, ingested, and combinations thereof. The effervescent composition can also be dissolved water of any suitable temperature. As the temperature of the water increases the amount and rate of evolution of vapors from the resulting aqueous effervescent composition tends to increase.

The liquid can be stirred to facilitate dispersion and/or dissolution of the effervescent composition in the aqueous liquid.

The invention will now be described by way of the following examples.

EXAMPLES

Hardness Test Method

The hardness of a tablet is determined using a Schlueniger hardness tester (Schlueniger Germany). Pressure is applied until the tablet breaks. The hardness is recorded in kilopounds (kp).

Clarity of Solution

A tablet is placed in a beaker that contains a sufficient amount of 40° C. water to dissolve the water soluble components of the tablet. The tablet is allowed to dissolve. The resulting liquid is observed with the naked eye for clarity, the presence of scum on the surface of the solution, and the presence of sediment on the bottom of the beaker. The observations are recorded.

Stability Test Method

Individually packaged tablets are stored in an oven at 45° C. and periodically observed for puffiness, i.e., visible expansion or puffing of the packaging relative to the packaged tablet immediately after manufacture.

Example 1

Menthol crystals USP (Nantong Menthol Factory, China) were passed through the #20 sieve screen of a RotorGran Machine (Manesty Machines Ltd., England) twice. The screened menthol crystals were then passed through a #20 sieve hand screen.

Into a Kitchen Aid mixer were sequentially added the following ingredients, all of which had been screened through a #20 sieve, with the exception of the sorbitol instant, which had been screened through a #12 sieve, prior to addition: 450 g sodium bicarbonate (powdered), 240 g sodium carbonate (grade 50), 48 g eucalyptus oil (Polarome International, Jersey City, N.J.), and 36 g of the above-processed menthol crystals USP (Nantong Menthol Factory, China). The composition was mixed on low speed for 15 minutes.

Then 600 g sorbitol instant FG (EM Industries, Darmstadt, Germany), 570 g citric acid (fine granular 50 USP/FCC), 0.9 g FD&C yellow No. 5 Aluminum Lake (Warner-Jenkinson, S. Plainfield, N.J.), and 0.51 g FD&C blue No. 1 Aluminum Lake (Warner-Jenkinson) were added to the above composition and the mixture was mixed for 15 additional minutes on low speed to form Composition B.

A portion (616 g) of Composition B was then combined with 21.85 g PEG 3350 polyethylene glycol (Dow Chemical Co., Midland, Mich.) and 15.2 g sodium benzoate (325 mesh) and mixed for 15 minutes on the low speed setting of a Kitchen Aid mixer.

The resulting composition was then formed into tablets, 21 millimeters in diameter, using a Kikusui tableting press to a target tablet hardness of from 6 kp to 10 kp, a target weight of 3.4 g and a target thickness of 0.26 inch. Individual tablets were then sealed in air tight foil packages and stored at room temperature.

After one month of storage at room temperature, a first set of packages was observed for stability. Two tablets were then removed from their respective packages and tested for hardness.

After just over one year of storage at room temperature a second set of packages was observed for stability. Three tablets were removed from their respective packages and tested for hardness.

The results and observations are reported in Table 1 in kilopounds (kp).

TABLE 1

| Tablet | Hardness after 1 month (kp) | Hardness after 1 year (kp) | Stability After One Month | Stability after one year |
|---|---|---|---|---|
| 1 | 25.2 | 29.3 | No puffing of the packaging was observed. | No puffing of the packaging was observed. |
| 2 | 26.6 | 25.0 | No puffing of the packaging was observed. | No puffing of the packaging was observed. |
| 3 | NA | 29.1 | NA | No puffing of the packaging was observed. |

The tablets were then placed in 40° C. tap water whereupon they dissolved in from 85 seconds to 130 seconds to form a green solution that was visibly clear. The clarity of the solution was determined by viewing with the naked eye. The solution was observed to be free of particulate matter suspended in the liquid, free of scum floating on top of the liquid and free of precipitation on the bottom of the clear glass container.

A tablet prepared according to Example 1 that had been stored for one year was placed in 125 mL of 40° C. tap water and allowed to dissolve. The tablet was observed to dissolve to a clear solution as determined by viewing with the naked eye. The solution was also observed to be free of particulate matter suspended in the liquid, free of scum floating on top of the liquid and free of precipitation on the bottom of the clear glass container.

TABLE 2

| Tablet | Dissolution Time (seconds) | Observations |
|---|---|---|
| 1 | 117 | Clear solution; good aroma |
| 2 | 130 | Clear solution; good aroma |

A second set of the packaged tablets prepared according to Example 1 is stored in an oven at 45° C. and observed after 7 hours, 3 days, 4 days, 5 days and 19 days of storage. The packages are observed to be free of puffing after each period.

Comparative Example

A package containing a PHYZZ STEAMWORKS sinus soothing mist tablet (lot 2031) (Phyzz, Inc., Cincinnati, Ohio) was obtained. The package for the PHYZZ STEAMWORKS tablet indicated that the tablet includes natural eucalyptus, camphor, and menthol. The package appeared to be inflated, indicating that carbon dioxide gas had been liberated from the tablet. The PHYZZ STEAMWORKS tablet was observed to be softer and less durable than the tablet of Example 1. The PHYZZ STEAMWORKS tablet crumbled when a portion of the tablet was removed for analysis.

A 3.5 g sample of the PHYZZ STEAMWORKS tablet was broken off from the tablet, weighed and placed in a clear plastic cup containing 125 ml of 40° C. tap water.

At the same time a tablet prepared according to Example 1 was tested under the same conditions as the Comparative Example.

The dissolution time and the appearance of the resulting composition for the Comparative Example and Example 1 are set forth in Table 3.

TABLE 3

| Tablet | Dissolution Time (seconds) | Appearance of Liquid |
|---|---|---|
| Comparative 1 | 60 | Cloudy blue liquid. Sediment was present on the bottom of the cup and scum was present on the surface of the liquid. |
| Example 1 | 93 | Clear green solution. The solution was free of scum and sediment. |

Other embodiments are within the claims. Although the composition has been described as forming a visibly clear solution in hot tap water, the effervescent composition can include components that produce an aqueous composition that is other than clear. Such components include, e.g., components that are water insoluble, slightly soluble in water, and combinations thereof. When such an effervescent composition is contacted with water, the resulting aqueous composition may be other than a solution including, e.g., a dispersion.

What is claimed is:

1. A tablet comprising an effervescent composition comprising:
   from 0.5% by weight to about 10% by weight menthol;
   from 0.5% by weight to about 10% by weight eucalyptus oil; and
   an effervescent agent comprising an acid and a base;
   wherein the tablet dissolves in water having a temperature of at least 38° C. to form a clear solution.

2. The tablet of claim 1, wherein said composition comprises from 1% by weight to about 5% by weight menthol.

3. The tablet of claim 1, wherein said composition comprises from 1% by weight to about 7% by weight eucalyptus oil.

4. The tablet of claim 2, wherein said composition comprises from 1% by weight to about 7% by weight eucalyptus oil.

5. The tablet of claim 1 having a hardness of at least 5 kilopounds.

6. The tablet of claim 1 having a hardness of at least 15 kilopounds.

7. The tablet of claim 1 having a hardness of at least 20 kilopounds.

8. The tablet of claim 1, wherein said tablet dissolves in water having a temperature of about 38° C. in less than 120 seconds.

9. The tablet of claim 1, wherein said tablet dissolves in water having a temperature of about 38° C. in less than 100 seconds.

10. The tablet of claim 6, wherein said tablet dissolves in water having a temperature of about 38° C. in less than 120 seconds.

11. The tablet of claim 6, wherein said tablet dissolves in water having a temperature of about 38° C. in less than 100 seconds.

12. The tablet of claim 1, further comprising lubricant.

13. The tablet of claim 12, wherein said lubricant comprises sodium benzoate, polyethylene glycol, L-leucine, adipic acid, or a combination thereof.

14. The tablet of claim 1, further comprising magnesium oxide.

15. The tablet of claim 1, further comprising pigment.

16. The tablet of claim 1, further comprising flavor agent.

17. The tablet of claim 1, further comprising sweetening agent.

18. The tablet of claim 1, further comprising sorbitol.

19. A tablet comprising an effervescent composition comprising:
   from 0.5% by weight to about 10% by weight menthol;
   from 0.5% by weight to about 10% by weight eucalyptus oil; and
   an effervescent agent comprising an acid and a base;
   the tablet having a hardness of at least 10 kilopounds and dissolving in water having a temperature of about 38° C. in less than 120 seconds.

20. The tablet of claim 19, wherein said tablet dissolves in water having a temperature of about 38° C. in less than 100 seconds.

21. The tablet of claim 19 having a hardness of at least 15 kilopounds.

22. The tablet of claim 19 having a hardness of at least 20 kilopounds.

23. The tablet of claim 21, wherein said tablet dissolves in water having a temperature of about 38° C. in less than 100 seconds.

24. The tablet of claim 22, wherein said tablet dissolves in water having a temperature of about 38° C. in less than 100 seconds.

25. A package comprising
air tight sealed packaging; and
the tablet of claim 1 disposed in said sealed packaging.

26. The package of claim 25, wherein said package is free of puffing after storage at 45° C. for 24 hours.

27. An effervescent composition comprising:
menthol;
eucalyptus oil; and
an effervescent agent comprising an acid and a base,
the composition dissolving in water having a temperature of about 38° C. to form a clear solution.

28. A powder comprising the effervescent composition of claim 27.

29. A carbonated mouthwash comprising:
water;
menthol; and
eucalyptus oil.

30. A method of forming an aqueous effervescent composition, said method comprising dissolving the tablet of claim 1 in water.

31. A method of using the tablet of claim 1, said method comprising
dissolving the tablet of claim 1 in water to form a clear solution; and
inhaling vapors emitted by the solution.

32. A method of using the tablet of claim 1, said method comprising
dissolving the tablet of claim 1 in water to form a clear solution; and
gargling with said solution.

33. The method of claim 31, wherein said water is at a temperature of at least 38° C.

34. The method of claim 31, wherein said water is boiling water.

\* \* \* \* \*

UNITED STATES PATENT AND TRADEMARK OFFICE
CERTIFICATE OF CORRECTION

| | | |
|---|---|---|
| PATENT NO. | : 7,815,897 B1 | Page 1 of 1 |
| APPLICATION NO. | : 10/743118 | |
| DATED | : October 19, 2010 | |
| INVENTOR(S) | : Wehling et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1909 days.

Signed and Sealed this
Fifteenth Day of February, 2011

David J. Kappos
*Director of the United States Patent and Trademark Office*